United States Patent [19]

Kane et al.

[11] 4,371,722

[45] Feb. 1, 1983

[54] CYCLIC TERPENOID AMINES, THEIR PREPARATION AND USES

[75] Inventors: Bernard J. Kane, Atlantic Beach; Richard A. Von Genk, Jacksonville, both of Fla.

[73] Assignee: SCM Corporation, New York, N.Y.

[21] Appl. No.: 277,815

[22] Filed: Jun. 26, 1981

Related U.S. Application Data

[62] Division of Ser. No. 130,374, Mar. 14, 1980, Pat. No. 4,307,255, which is a division of Ser. No. 860,284, Dec. 14, 1977, Pat. No. 4,244,890.

[51] Int. Cl.$^3$ .......... C07C 35/08

[52] U.S. Cl. .......... 568/828; 568/832; 568/834; 568/835; 568/833

[58] Field of Search .......... 568/828, 833, 834, 835, 568/875, 832; 560/832, 231, 248, 249; 564/281

[56] References Cited

U.S. PATENT DOCUMENTS

| | | | |
|---|---|---|---|
| 2,634,272 | 4/1953 | Hellenbach | 260/283 |
| 3,228,976 | 6/1968 | Heuber | 260/283 |
| 3,917,720 | 11/1975 | Webb | 560/248 |
| 3,932,539 | 1/1976 | Kane | 568/875 |
| 4,017,634 | 4/1977 | Lam et al. | 424/300 |
| 4,161,609 | 7/1979 | Cramer | 560/231 |
| 4,179,468 | 12/1979 | Kane | 564/281 |
| 4,244,890 | 1/1981 | Kane | 560/249 |
| 4,251,673 | 2/1981 | Mark et al. | 568/835 |
| 4,267,366 | 5/1981 | Kane et al. | 560/231 |
| 4,307,255 | 12/1981 | Kane et al. | 560/231 |

FOREIGN PATENT DOCUMENTS

| | | | |
|---|---|---|---|
| 52-48642 | 4/1977 | Japan | 568/828 |

OTHER PUBLICATIONS

Richer et al., "Chem. Abstract", vol. 70, (1969), p. 11181f.

Kokai, "Chem. Abstracts", vol. 87, p. 775, (1977).

Morie et al., "Tetrahedron", vol. 26, pp. 2815-2819.

Gabriel, "J. Organic Chem.", vol. 37, pp. 4036-4039, (1972).

Watanabe, "Australian J. Chem.", vol. 27, (1974), pp. 531-535.

*Primary Examiner*—Werren B. Lone

*Attorney, Agent, or Firm*—Robert A. Sturges; Merton H. Douthitt

[57] ABSTRACT

Disclosed are novel cyclic terpenoid amines which can be prepared by cyclizing the corresponding acyclic terpenoid amine.

8 Claims, No Drawings

CYCLIC TERPENOID AMINES, THEIR PREPARATION AND USES

CROSS-REFERENCE TO RELATED APPLICATIONS

This application is a divisional of our co-pending application Ser. No. 130,374 filed Mar. 14, 1980 now U.S. Pat. No. 4,307,255 which in turn was a divisional of our then co-pending application Ser. No. 860,284 filed Dec. 14, 1977 now U.S. Pat. No. 4,244,890 dated Jan. 13, 1981, which application was in turn related to our then co-pending application Ser. No. 916,866 filed June 19, 1978 now U.S. Pat. No. 4,179,468 dated Dec. 18, 1979, and then co-pending application Ser. No. 049,607 filed June 18, 1979, now U.S. Pat. No. 4,267,366 dated May 12, 1981.

BACKGROUND OF THE INVENTION

This invention relates to certain novel cyclic terpenoid amines, their preparation, and their uses.

While preparing unsaturated terpene alcohols according to the Kane and Von Genk process (U.S. Pat. No. 3,932,539), it was discovered unexpectedly that terpenoid amines subjected to the hydration step of such process were cyclized rather than hydrated when such hydration step was practiced at higher temperatures of above about 80° C. and advantageously above about 100° C. The novel cycloterpenoid amines disclosed herein are useful in the synthesis of fragrances and carotenoids, for example. In a preferred embodiment of the present invention, the cyclized amines can be converted into beta-cyclogeraniol and further into beta-cyclocitral for synthesis of beta-ionone and Vitamin A. Additionally, other novel cyclic terpenoid compounds, which are useful as fragrances and as intermediates in other synthesis work, are made during the above synthesis.

BROAD STATEMENT OF THE INVENTION

The cyclic terpenoid amines disclosed herein can be represented conventionally by the following general structures:

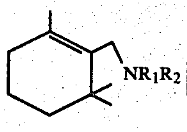
(I) Beta Isomer

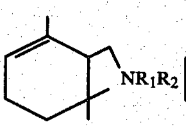
(II) Alpha Isomer

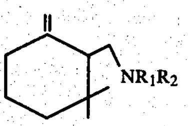
(III) Gamma Isomer where $R_1$ is hydrogen or a $C_{1-4}$ aliphatic group (advantageously a $C_{1-4}$ alkyl group), and $R_2$ is hydrogen or a monovalent radical, usually a monovalent organic radical; or $R_1$, $R_2$ are joined as a heterocyclic residue. Suitably monovalent radicals can be saturated, can contain unsaturation, and/or can be substituted with a wide variety of groups as disclosed herein. Advantageously, $R_2$ is a $C_{1-4}$ alkyl group.

Such cyclic terpenoid amines can be prepared from neryl/geranyl amines represented by $T_ANR_1R_2$, where $T_A$ is a neryl group or a geranyl group, by maintaining an acidic aqueous solution of the neryl/geranyl amine at a temperature of at least about 80° C. until cyclization occurs. In the reaction solution, there is at least 1.1 equivalents of acid per equivalent of the neryl/geranyl amine.

Also, cyclic terpenoid esters of carboxylic acids represented by the following general structure:

(IV)

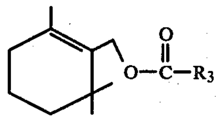

where $R_3$ is an aliphatic hydrocarbon and advantageously a $C_{1-4}$ alkyl group, can be prepared by reacting the foregoing cyclic terpenoid amines, which can be represented by $GNR_1R_2$, where G is the cyclogeranyl group, with a carboxylic acid anhydride at a temperature between about 70° and 250° C. until the cyclic ester is formed. A unique feature of this process is that only the beta-isomer (I) reacts to form the ester as the alpha and gamma isomers (II and III) do not react with the anhydride. The anhydride can be represented by the following structure:

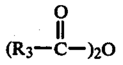
(V)

where $R_3$ is an aliphatic moeity or group.

A minor by-product of the cyclic terpenoid carboxylic acid ester process is "cyclolinalyl" ester of the carboxylic acid which can be represented conventionally by the following general structure:

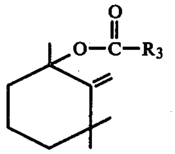
(VI)

where $R_3$ is an aliphatic hydrocarbon. The "cyclolinalyl" ester can be converted into "cyclolinalool" by a hydrolysis reaction. "Cyclolinalool" (1,3,3-trimethyl-2-methylene-1-cyclohexanol) can be represented conventionally as follows:

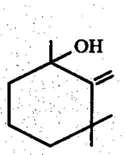
(VIII)

DETAILED DESCRIPTION OF THE INVENTION

The cycloterpenoid amines of the present invention are primary, secondary or tertiary amines containing the cyclogeranyl radical. A novel method of preparing such cyclic amines involves the cyclization of neryl/geranyl amine. Starting materials for this cyclization reaction may be prepared conveniently by reacting neryl/geranyl halide, preferably chloride, with a primary or secondary amine. In this reaction, the reactivity of the amine with the terpene chloride will depend upon electronic considerations and steric considerations. Some amines, particularly those connected to an aromatic system, e.g. N-methylaniline, are less readily alkylated by the terpene chloride than are aliphatic or benzylic amines. Also, rather large and bulky groups attached to the amine can be expected to sterically hinder the alkylation of the amine by the terpene chloride. One such unreactive, sterically hindered amine for this alkylation reaction is diisopropylamine. The starting amine, then, to be useful, must be alkylated at a reasonable rate by the neryl/geranyl chloride. Examples of suitable neryl/geranyl amines which can be prepared by this alkylation reaction, and subsequently cyclized, include:

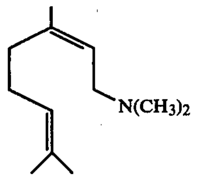

neryl dimethyl amine (VIIIa)

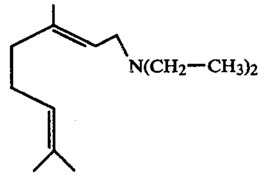

geranyl diethyl amine (VIIIb)

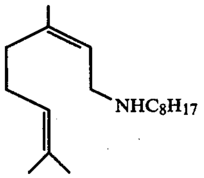

neryl octanyl amine (IX)

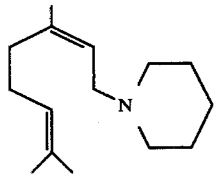

neryl piperidyl amine (X)

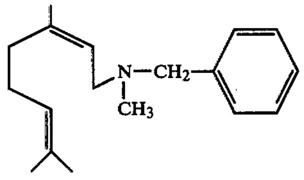

N—neryl-N—methylbenzylamine (XI)

Alternatively, terpene dialkylamines can be prepared by the addition of a secondary amine, such as diethylamine or the like, directly to myrcene in the presence of special catalysts such as sodium naphthalenide according to the process proposed by Watanabe et al. in the *Australian Journal of Chemistry,* 1974, Volume 27, Pages 531-535. Also, N,N-diethylnerylamine may be prepared by the telomerization of isoprene with diethylamine in the presence of n-butyl-lithium catalyst according to the process of Takabe et al., *Tetrahedron Letters,* No. 34, Pages 3005-3006, 1975. Geranyl/neryl amines may be prepared additionally by the reduction of citral oxime as taught in U.S. Pat. No. 4,017,634, or by the Gabriel synthesis as described in the *Journal of Organic Chemistry,* 1972, Volume 37, Pages 4036-4039. The disclosures of the foregoing references are incorporated herein expressly by reference.

Regardless of how the terpenoid amines are prepared, cyclization is practiced by maintaining an acidic aqueous solution of the terpenoid amine until cyclization occurs. At least 1.1 equivalents of acid per equivalent of said amine salt is used in this reaction, advantageously at least about 2 equivalents of acid, and preferably about 2 to 3 equivalents of the acid. While more than 3 equivalents of the acid can be used, such amounts tend to be less convenient to handle and more costly to use. Typically, about a 20% to 30% acid concentration in the aqueous solution will be found to be useful for the instant cyclization reaction. Appropriate acids for this reaction include, for example, hydrochloric acid, sulfuric acid, phosphoric acid, hydrobromic acid, and the like. The cyclization reaction preferably is carried out at temperatures above about 80° C., usually between about 80° and 120° C., preferably under reflux conditions. Temperatures higher than 120° C. can be practiced and are advantageous for faster reaction rates; however, this would require use of pressurized equipment for conducting the reaction. Temperatures of about 100°-120° C. are quite useful when a 20% to 30% acid concentration is maintained in the reaction solution. Inert solvents such as ethers, cellosolves, and the like can be used as is necessary or desirable.

The progress of the cyclization reaction can be followed conveniently by periodic removal and analysis of samples from the reaction solution. The cyclized amine product usually is a mixture of alpha, beta, and gamma cyclogeranyl isomers with the beta isomer form usually predominating with extended times of reaction. The cyclized terpenoid amines can be liberated conveniently from the reaction mixture by neutralization of the reaction solution with a suitable base, such as an alkali metal hydroxide or the like. Further purification of the cyclic amine products by fractional distillation or fractional crystallization can be practiced conventionally as desired or required.

The following are additional examples of neryl/geranyl amines which can be expected to cyclize according to the instant cyclization process:

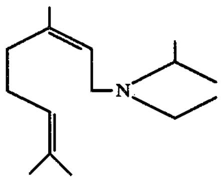

N—ethyl-N—2-propyl nerylamine (XII)

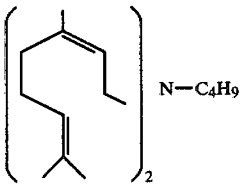

dinerylbutyl amine (XIII)

A prime use of the instant cyclic terpenoid amines is in the preparation of beta-cycloterpenoid esters of carboxylic acids [Structure (IV)]. This process reacts the cyclic tertiary amines with a carboxylic acid anhydride at about 70° to 250° C., advantageously about 100° to 180° C., and preferably about 100° to 120° C., until the cycloterpenoid ester is formed. Typically, the molar ratio of anhydride to cyclic tertiary amine is from about 0.2 to 20, and preferably from about 1 to 3. Appropriate carboxylic acid anhydrides can be represented conventionally as follows:

$$(R_3-\overset{\overset{O}{\|}}{C}-)_2O \qquad (V)$$

where $R_3$ is an aliphatic group or moeity. This reaction is performed generally according to that procedure disclosed in Japanese Kokai 116411/75, the disclosure of which is incorporated herein by reference. This general procedure also is reported by Fujita et al. in *Aust. J. Chem.;* 1974, 27, 531-535, which is incorporated herein expressly by reference. A unique feature of this process is that the alpha and gamma-cyclogeranyl amines are virtually unreactive and, surprisingly, essentially only the beta- form ester results. Consequently, the isomer mixture of cyclic amines need not be purified rigorously for separation of the pure beta isomer. Instead, the unreacted alpha and gamma isomers can be isomerized to produce an equilibrium mixture rich in the beta isomer for admission to the process to form more of the ester. Illustrative of the foregoing reaction is the production of beta-cyclogeranyl acetate as follows:

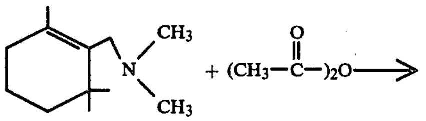

beta-Cyclogeranyl Dimethylamine

Acetic Anhydride

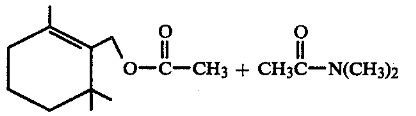

beta-Cyclogeranyl Acetate

Dimethylacetamide

Of course, primary and secondary beta-cyclogeranyl amines can be used in the foregoing ester formation reaction provided that they are first alkylated to a tertiary amine with an appropriate alkylating agent, such as an alkyl halide or an alkyl sulfate, for example.

The foregoing beta-cycloterpenoid esters can be conventionally saponified with alkali, for example, to replace the ester group with the hydroxyl group, i.e. produce beta-cyclogeranoil. Reaction conditions for this saponification reaction include temperatures of about 80° C. to about 140° C. and use of about 1.05 to 2.0 moles of alkali metal hydroxide of about 5% to 50% concentration in water. Beta-cyclogeraniol is an especially valued product since it can be oxidized to beta-cyclocitral which is useful in the synthesis of beta-ionone, Vitamin-A, and various carotenoids. The oxidation of beta-cyclogeraniol to beta-cyclocitral can be performed according to the Ehmann process as described in commonly assigned copending application Ser. No. 682,113 of May 30, 1975. Beta-cyclocitral is useful in the synthesis of Vitamin A according to the Mukaiyama et al process reported in *Chemistry Letters,* pp. 1201-1202, 1975 (The Chemical Society of Japan). Beta-cyclogeraniol also can be converted into Vitamin A through the Wittig route according to the procedure outlined by Pommer in *Angew. Chem. International Edition/Sample Issue,* pages 31-40 (1960). The above references are incorporated herein expressly by reference.

A minor by-product formed by the reaction of beta-cyclogeranyl dimethylamine with acetic anhydride (as outlined above), is "cyclolinalyl acetate" which can be hydrolyzed with acid or base into "cyclolinalool". These products can be represented as follows:

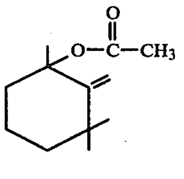

Cyclolinalyl Acetate (VIa)

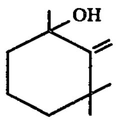

Cyclolinalool (VII)

Both of the foregoing compounds can have uses as fragrances and as intermediates in the synthesis of cartenoids, for example. Consequently, a new class of compounds, "cyclolinalyl" esters of carboxylic acids and the corresponding alcohol, "cyclolinalool", are encompassed within the scope of the present invention.

The following Examples show in detail how the present invention can be practiced but should not be construed as limiting. In this application, all temperatures are in degrees Centigrade and all percentages are weight percentages, unless otherwise expressly indicated.

EXAMPLE 1

Preparation of Neryl/Geranyl Dimethylamine

One thousand two hundred twenty grams of beta-pinene pyrolysate, containing approximately 75% myrcene, was converted to a mixture of neryl/geranyl chlorides by hydrochlorination of the pyrolysate at 0° C. in the presence of cuprous chloride catalyst. The reaction consumed about 280 grams of hydrogen chloride. One thousand five hundred thirty-nine grams of 40% aqueous dimethylamine was added to 1500 grams of the myrcene hydrochlorination product at 18°-25° C. over a period of 2 hours. The reaction mixture was held at 20°-25° C. for an additional 4 hours under stirring, followed by the addition of 500 grams of 50% aqueous sodium hydroxide solution. The reaction mixture then was heated at 90° C. to drive off excess dimethylamine and the reaction mixture cooled. The cooled reaction mixture separated into a lower aqueous phase and an upper oil pase. The two phases were separated and the recovered oil phase weighing 1635 grams was determined to contain approximately 60% of product neryl/geranyl dimethylamine. The recovered oil layer then was distilled under reduced pressure and 720 grams of purified neryl/geranyl dimethylamine of 91% purity was recovered.

EXAMPLE II

Cyclization of Neryl/Geranyl Dimethylamine

To 520 grams of a 19% aqueous hydrochloric acid solution was added 250 grams of neryl/geranyl dimethylamine. The homogeneous solution was heated at about 90° C. and samples of the solution were periodically removed for analysis. The samples were analyzed by treatment with excess sodium hydroxide solution followed by gas chromatographic analysis of the oil phase. The following table summarizes the progress of the cyclization reaction over the course of the reaction.

| GC Analysis | Hour: | | | | | | |
|---|---|---|---|---|---|---|---|
| (weight percent) | 1 | 2 | 4 | 8 | 16 | 32 | 64 |
| alpha-Cyclogeranyl | 23.5 | 37.9 | 39.5 | 35.3 | 25.0 | 23.2 | 23.0 |

-continued

| GC Analysis (weight percent) | Hour: 1 | 2 | 4 | 8 | 16 | 32 | 64 |
|---|---|---|---|---|---|---|---|
| Dimethylamine | | | | | | | |
| beta-Cyclogeranyl Dimethylamine | 3.4 | 6.8 | 17.7 | 30.5 | 47.5 | 51.2 | 52.3 |
| gamma-Cyclogeranyl Dimethylamine | 20.8 | 19.7 | 15.1 | 12.7 | 10.1 | 8.4 | 8.0 |
| Uncyclized Amine & Unknowns | 11.9 | 11.4 | 10.7 | 10.8 | 10.6 | 10.8 | 9.7 |
| Amino Alcohols | 3.1 | 23.0 | 14.0 | 8.39 | 6.3 | 5.7 | 6.2 |

After 64 hours of reaction time, the reaction mixture was made basic by the addition of 250 grams of 50% aqueous sodium hydroxide solution. The oil layer which formed was separated and fractionally distilled at reduced pressure to yield a distillate of beta-cyclogeranyl dimethylamine of about 90% purity. The structure of the beta-cyclogeranyl dimethylamine was confirmed by NMR (nuclear magnetic resonance) analysis.

EXAMPLE III

Cyclization of Neryl/Geranyl Dimethylamine

To 640 grams of a 20% aqueous hydrochloric acid solution was added 250 grams of neryl/geranyl dimethylamine. The solution was heated at 100° C. for 16 hours, after which the cyclogeranyl amine products were recovered from the solution. Gas chromatographic analysis of the product indicated that the beta-cyclogeranyl dimethylamine content was about 52.8% and that the reaction was substantially complete.

The reaction was repeated as above indicated, except that the aqueous acid used was 400 grams of 19% aqueous hydrochloric acid. After a reaction time of 32 hours, it was determined that the beta-cyclogeranyl dimethylamine content of the product was 51% and that the reaction was substantially complete.

EXAMPLE IV

Preparation and Cyclization of Neryl/Geranyl Dimethylamine

Neryl/geranyl dimethylamine was prepared by bubbling anhydrous dimethylamine gas (404 grams) through 1500 grams of myrcene hydrochloride (from Example 1) over a 4 hour period at a temperature of 30°-35° C. At the end of the addition, there was added 400 grams of water and 800 cc of a 37% hydrochloric acid solution. The reaction was cohobated for about 24 hours. The cohobated oil weighed 373 grams. Gas chromatographic analysis indicated that the oil was primarily a mixture of terpene hydrocarbons. The solution was made basic by the addition of 865 grams of 50% aqueous sodium hydroxide solution. The reaction was cohobated again. 526 grams of oil was recovered from the reaction mixture and subjected to gas chromatographic analysis. The oil was determined to contain 23% alpha-cyclogeranyl dimethylamine, 53% beta-cyclogeranyl dimethylamine, 10% gamma-cyclogeranyl dimethylamine, 2% amino alcohols, and 12% miscellaneous compounds.

EXAMPLE V

Preparation of Neryl/Geranyl Dibutylamine

Seven hundred forty grams of myrcene hydrochloride (prepared as described in Example 1) was added gradually over a one hour period to 488 grams of dibutylamine at 70°-75° C. The reaction mixture was held at this temperature for 2 hours and then 750 grams of 15% aqueous sodium hydroxide solution added thereto. The neutralized reaction mixture was refluxed for an additional 4 hours. The oil phase, after separation, weighed 1011 grams and by gas chromatographic analysis was determined to contain 63.8% neryl/geranyl dibutylamine. The crude cyclic amine product was distilled and a main fraction obtained at 102°-104° C. at 0.4 mm pressure. This fraction weighed 577 grams and was determined to be 98% pure neryl/geranyl dibutylamine.

EXAMPLE VI

Cyclization of Neryl/Geranyl Dibutylamine

Two hundred sixty-five grams of neryl/geranyl dibutylamine from Example V was added to a solution of 465 grams of 16% aqueous hydrochloric acid and refluxed for 35 hours. The solution then was cooled and neutralized by the addition of 200 grams of 50% aqueous sodium hydroxide solution. Gas chromatographic analysis of the liberated oil phase indicated that the content of beta-cylogeranyl dibutylamine was 45.3%. The cyclic amine products were fractionally distilled at reduced pressure and the structure of products confirmed by NMR analysis.

EXAMPLE VII

Conversion of beta-Cyclogeranyl Dibutylamine to beta-Cyclogeranyl Acetate

A 5 gram fraction containing 46.3% beta-cyclogeranyl dibutylamine and 53.7% of alpha- and gamma-cyclogeranyl dibutylamine was reacted with 9 grams of acetic anhydride at 130° C. for about 50 hours. Gas chromatographic analysis of the product indicated that only the beta-isomer reacted to give beta-cyclogeranyl acetate with some gamma-pyronene also being formed. The alpha- and gamma-cyclogeranyl dibutylamine isomers were substantially unreacted.

EXAMPLE VIII

Preparation of Mono and Di-Neryl/Geranyl Monobutylamine

Seven hundred forty grams of myrcene hydrochloride was reacted with 220 grams of n-butylamine at 65°-70° C. for 2 hours, the reaction mixture neutralized with sodium hydroxide, and then refluxed for an additional 4 hours. The separated oil phase was purified by fractional distillation to give 133 grams of neryl/geranyl monobutylamine and 245 grams of di-neryl/geranyl monobutylamine.

EXAMPLE IX

Cyclization of Neryl/Geranyl Monobutylamine

Twenty-five grams of neryl/geranyl monobutylamine was added to 50 grams of 18% aqueous hydrochloric acid solution and the mixture refluxed at 105° C. for 6.5 hours. Addition of 25 grams of 50% aqueous sodium hydroxide solution liberated 24 grams of cyclized product, which by gas chromatographic analysis was determined to contain: 50% beta-cyclogeranyl monobutylamine and lesser amounts of corresponding alpha and gamma isomers. Fractional distillation resulted in a purified beta-cyclogeranyl monobutylamine product, which structure was confirmed by NMR analysis.

EXAMPLE X

Fifty grams of a fraction containing 90% beta-cyclogeranyl dimethylamine, 2% alpha-cyclogeranyl dimethylamine, 4.9% gamma-cyclogeranyl dimethylamine, and 2% related cyclic isomers was heated with 93 grams of acetic anhydride at 110°–115° C. for 3 hours. The reaction mixture was neutralized with sodium hydroxide and the recovered product subjected to gas chromatographic analysis. The following composition of the product was determined: 3.4% delta-pyronene, 35% gamma-pyronene, 1.7% alpha-cyclogeranyl dimethylamine, 0.4% beta-cyclogeranyl dimethylamine, 5.9% gamma-cyclogeranyl dimethylamine, 3.1% other cyclic amines, 4.3% "cyclolinalyl acetate", and 44.5% beta-cyclogeranyl acetate.

The foregoing crude reaction product mixture was washed with sodium hydroxide solution, saponified by refluxing with 50% aqueous sodium hydroxide solution, and then distilled at reduced pressure. The structures of purified fractions of "cyclolinalool" and beta-cyclogeraniol were confirmed by NMR analysis.

EXAMPLE XI

Isomerization of alpha- and gamma-Cyclogeranyl Dimethylamines to beta-Cyclogeranyl Dimethylamine Two hundred twenty-seven grams of a mixture of 36% beta-cyclogeranyl dimethylamine, 50% alpha-cyclogeranyl dimethylamine, and 11% gamma-cyclogeranyl dimethylamine was refluxed with 565 grams of a 19% aqueous hydrochloric acid solution for 36 hours. The reaction mixture was made basic by the addition of 300 grams of 50% aqueous sodium hydroxide solution. The recovered oil phase weighed 225 grams and by gas chromatographic analysis, was determined to contain 70% beta-cyclogeranyl dimethylamine, 15% alpha-cyclogeranyl dimethylamine, and 8% gamma-cyclogeranyl dimethylamine.

EXAMPLE XII

Cyclization of Neryl/Geranyl Dimethylamine

Twenty-five grams of neryl/geranyl dimethylamine were heated at 90% C. with the solution of 104 grams of 13% aqueous sulfuric acid solution for 64 hours. Gas chromatographic analysis of the separated and neutralized oil phase indicated that the following products were present: 29% alpha-cyclogeranyl dimethylamine, 2.2% beta-cyclogeranyl dimethylamine, 26.8% gamma-cyclogeranyl dimethylamine, 7.7% unknown cyclic amines, and 33.5% amino alcohols. The lower conversion of neryl/geranyl dimethylamine to product beta-cyclogeranyl dimethylamine probably resulted from the lower concentration of sulfuric acid used in this reaction.

EXAMPLE XIII

Conversion of beta-Cyclogeraniol to beta-Ionone

The first step is the oxidation of beta-cyclogeraniol to beta-cyclocitral according to the process of William J. Ehmann in Ser. No. 582,113, cited above. Three grams of 99% pure beta-cyclogeraniol was heated at 40°–45° C. with a solution of 5 grams of furfural, 7 milliliters of benzene, and 1 gram of aluminum isopropoxide catalyst. After three hours of reaction time, gas chromatographic analysis of the reaction mixture indicated the following composition: 31% furfural, 21% furfuryl alcohol, 26% beta-cyclocitral, and 11% beta-cyclogeraniol.

To the reaction mixture then was added 70 grams acetone, 2.5 grams sodium hydroxide, and 25 grams methanol. The reaction mixture was stirred at 40°–45° C. for about 2 hours; 5 cc of acetic acid then was added to neutralize the sodium hydroxide catalyst. Analysis of the crude reaction product mixture indicated the following products: 20% furfuryl alcohol, 9% beta-cyclogeraniol, 49% furfural-acetone condensation products, and 22% of the desired beta-ionone product.

The crude reaction product was distilled under reduced pressure and the presence of beta-ionone was confirmed by infrared and mass spectroscopy analysis of the resulting distillation fractions.

EXAMPLE XIV

Preparation of Neryl/Geranylamine and its Cyclization

The starting geranylamine was prepared by reduction of citral oxime with lithium aluminum hydride reagent. The purified amine contained 26% of the neryl- and 66% of the geranyl-isomer. To 11.9% g of 17% hydrochloric acid solution was added 4.5 g of the neryl/-geranylamine. This homogeneous solution was refluxed at 107° C. After one hour, a sample was removed and the amine product liberated by the addition of 10% sodium hydroxide solution. Gas chromatographic analysis indicated a ratio of 65% beta-cyclogeranylamine to 35% of the alpha- and gamma-isomers. After 8 hours reaction, the ratio determined by gas chromatography was 75% of the beta-cyclogeranylamine and 25% of the alpha- and gamma-isomers. The cyclogeranylamine was isolated from the reaction by steam distillation after the addition of sufficient 10% sodium hydroxide solution to render the reaction mixture strongly basic.

The product was then analyzed by NMR, which confirmed the presence of alpha-, beta- and gamma-cyclogeranylamines.

We claim:

1. A process for making 1,3,3-trimethyl-2-methylene-cyclohexan-1-ol which comprises maintaining an acidic aqueous solution of an acyclic terpenoid group-containing amine represented by $$T_ANR_1R_2$$

where $T_A$ is a neryl group or a geranyl group, $R_1$ is a $C_1$–$C_4$ aliphatic group, $R_2$ is a monovalent organic group, or $R_1$ and $R_2$ are joined together and with N as a cyclic group, at a temperature of at least about 80° C., until said acyclic terpenoid group cyclizes, there being at least about 1.1 equivalents of acid per equivalent of said amine in said solution; recovering a mixture of alpha-, beta-, and gamma-cyclogeranylamines, reacting said mixture of amines with a carboxylic acid anhydride at about 70° C. to 250° C. to selectively form a beta-cyclogeranyl ester of a carboxylic acid and, as a by-product formed during said reaction, the cyclolinalyl ester of a carboxylic acid, recovering separately said beta-cyclogeranyl ester of a carboxylic acid, unreacted alpha-, and gamma-cyclogeranyl amines, and the cyclolinalyl ester of said carboxylic acid, and hydrolyzing the recovered cyclolinalyl ester by heating in the presence of an aqueous solution of an acid or a base to form 1,3,3-trimethyl-2-methylene-cyclohexan-1-ol.

2. The process of claim 1 wherein said temperature is between about 80° C. and 120° C. and at least about 2 equivalents of acid are used.

3. The process of claim 1 wherein $R_1$ and $R_2$ independently are a $C_{1-4}$ alkyl group.

4. The process of claim 1 wherein said carboxylic acid anhydride is an anhydride of an aliphatic carboxylic acid.

5. The process of claim 1 wherein said recovered alpha-, and gamma-cyclogeranylamines are maintained in an acidic aqueous reaction mixture at a temperature of at least about 80° C. to isomerize at least a fraction of said alpha- and gamma-cyclogeranylamines into beta-cyclogeranylamine, and the resulting isomerizate is returned for reaction with said carboxylic acid anhydride.

6. The process of claim 9 wherein said cyclolinalyl ester of a carboxylic acid is represented by

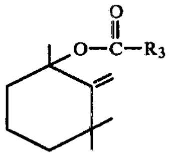

where $R_3$ is a $C_{1-4}$ alkyl group.

7. The process of claim 1 wherein said recovered beta-cyclogeranyl ester of a carboxylic acid is saponified with a base to form cyclogeraniol.

8. The process of claim 7 wherein said beta-cyclogeranyl ester of a carboxylic acid is represented by

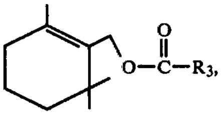

where $R_3$ is a $C_{1-4}$ alkyl group.

* * * * *

UNITED STATES PATENT AND TRADEMARK OFFICE
CERTIFICATE OF CORRECTION

PATENT NO. : 4,371,722

DATED : 1 February 1983

INVENTOR(S) : Bernard J. Kane and Richard A. Von Genk

It is certified that error appears in the above-identified patent and that said Letters Patent are hereby corrected as shown below:

Column 11, line 6, claim 6, change the numeral "9" to ---1---.

Signed and Sealed this

*Fourteenth* Day of *June 1983*

[SEAL]

*Attest:*

DONALD J. QUIGG

*Attesting Officer* *Acting Commissioner of Patents and Trademarks*